(12) United States Patent
Korzekwa et al.

(10) Patent No.: US 6,625,547 B1
(45) Date of Patent: Sep. 23, 2003

(54) RELATIVE RATES OF CYTOCHROME P450 METABOLISM

(75) Inventors: Kenneth R. Korzekwa, Mountain View, CA (US); Jeffrey P. Jones, Pullman, WA (US)

(73) Assignees: Washington State University Research Foundation, Pullman, WA (US); ArQule, Inc., Woburn, MA (US)

(*) Notice: Subject to any disclaimer, the term of this patent is extended or adjusted under 35 U.S.C. 154(b) by 0 days.

(21) Appl. No.: 09/613,875

(22) Filed: Jul. 10, 2000

Related U.S. Application Data

(63) Continuation-in-part of application No. 09/368,511, filed on Aug. 5, 1999.
(60) Provisional application No. 60/095,460, filed on Aug. 5, 1998.

(51) Int. Cl.[7] .......................... G06G 7/58; G06F 9/455
(52) U.S. Cl. ........................... 702/22; 702/30; 703/2
(58) Field of Search .................... 702/22, 30; 435/7.91, 435/25; 424/435; 703/2

(56) References Cited

FOREIGN PATENT DOCUMENTS

| WO | WO 95/18969 | 7/1995 |
|---|---|---|
| WO | WO00/08205 | 2/2000 |

OTHER PUBLICATIONS

Bradford, M. M., et al., "A Rapid and Sensitive Method for the Quantitation of Microgra Quantities of Protein Utilizing the Principle of Protein–Dye Binding," Anal. Biochem., (1976) 72:248–54.
Burka, L. T., et al., "Mechanism of Cytochrome P–450 Catalysis. Mechanism of N–Dealkylation and Amine Oxide Deoxygenation," J. Am. Chem. Soc., (1985) 107:2549–51.
Burka, L. T., et al., "Mechanisms of Hydroxylation by Cytochrome P–450: Metabolism of Monohalobenzenes by Phenobarbital–Induced Microsomes," Proc. Natl. Acad. Sci. USA (1983) 80:6680–4.
Cleland, W. W., "Partition Analysis and the Concept of Net Rate Constants as Tools in Enzyme Kinetics," Biochemistry, (1975) 14(14):3220–4.
Cleland, W. W., "The Use of Isotope Effects to Determine Transition–State Structure for Enzymic Reactions," Methods Enzymol., (1982) 87:625–41.
Cupp–Vickery, J.R. et al., "Structure of Cytochrome P450eryFInvolved in Erythromycin Biosynthesis," Structural Biology, (1995) 2(2):144–53.
Dinnocenzo, J. P., et al., "On Isotope Effects for the Cytochrome P–450 Oxidation of Substituted NN–Dimethylanilines," J. Am. Chem. Soc.,(1993) 115:7111–6.
Franchetti, P., et al., "Furanfurin and Thiophenfurin: Two Novel Tiazofurin Analogues. Synthesis, Structure, Antitumor Activity, and Interactions with Inosine Monophosphate Dehydrogenase," J. Med. Chem., (1995) 38:3829–37.

Gonzalez, F. J., et al., "Human Cytochromes P450: Problems and Prospects," TIPS Reviews, (1992) 13:346–52.
Gonzalez, F.J., et al., "Expression ofMammalian Cytochrome P450 Using Paccinia Virus," Methods Enzymol., (1991) 206:85–92.
Grogan, J., et al., "Modeling Cyanide Release from Nitriles: Prediction of Cytochrome P450 Mediated Acute Nitrile Toxicity," Chem. Res. Toxicol., (1992) 5(4):548–52.
Groves, J. T., et al., "Aliphatic Hydroxylation by Highly Purified Liver Microsomal Cytochrome P–450. Evidence for a Carbon Radical Intermediate," Biochemical & Biophysical Research Communications (1978) 81(1):154–60.
Groves, J.T., et al., "Hydroxylation by Cytochrome P–450 and Metalloporphyrin Models. Evidence for Allylic Rearrangement," J. Am. Chem. Soc., (1984) 106:2177–81.
Guengerich, F. P., et al., "Role of Human Cytochrome P–450 IIEI in the Oxidation of Many Low Molecular Weight Cancer Suspects," Chem. Res. Toxicol., (1991) 4:168–79.
Guengerich, F. P., et al., "Evidence for a 1–Electron Oxidation Mechanism in N–Dealkylation ofN,N–Dialkylanilines by Cytochrome P450 2B1," J. Biol. Chem., (1996) 271(44):27321–9.
Hammond, G. S., "A Correlation ofReaction Rates," J. Am. Chem. Soc., (1955) 77(2):334–40.
Hanzlik, R.P., et al., "Intramolecular Kinetic Deuterium Isotope Effects on Microsomal Hydroxylation and Chemical Chlorination of Toluene–a–dl and Toluene–a,a–d2," J. Am. Chem. Soc., (1985) 107:7164–7.
Harada, N., et al., "Kinetic Isotope Effects on Cytochrome P–450–Catalyzed Oxidation Reaction," J. Biol. Chem., (1984) 259(5):3005–10.
Hasemarm, C.A., et al., "Structure and Functions of Cytochromes P450: A Comparative Analysis of Three Crystal Structures," Structure, (1995) 3(1):41–62.
Hasemann, C.A., et al., "Crystal Structure and Refinement of Cytochrome P450terp at 2–3 A Resolution," J. Mol. Biol., (1994) 236:1169–85.
Heberger, K., "Linear Free Energy Relationships in Radical Reactions. II Hydrogen Abstraction From Substituted Toluenes by TERT–Butyl, TERT–Butoxyl and Tert–Butylperoxyl Radicals," J. Phys. Org. Chem., (1994) 7:244–50.

(List continued on next page.)

Primary Examiner—Marjorie Moran
(74) Attorney, Agent, or Firm—Beyer Weaver & Thomas, LLP

(57) ABSTRACT

Reactive sites on a substrate molecule, typically a drug, may be identified and the relative rates of their metabolism by the CYP enzymes may be determined. Determining these relative rates is an important factor in determining the absolute rate of metabolism of the individual sites and the substrate molecule as a whole. This information is also a critical factor in determining whether and how the substrate can be redesigned to improve its ADME/PK properties. In this regard, it is particularly important to know how the relative rates compare to the rate of a non-metabolic side reaction (branch pathway) such as water generation and regeneration of the substrate.

25 Claims, 10 Drawing Sheets

OTHER PUBLICATIONS

Hermes, J.D., et al., "Use of Multiple Isotope Effp.,s to Determine Enzyme Mechanisms and Intrinsic Isotope Effects. Malic Enzyme and Glucose–6–phosphate Dehydrogenase," Biochemistry, (1982) 21:5106–1428.

Hjelmeland, L. M., et al., "Intramolecular Determination of Primary Kinetic Isotope Effects in Hydroxylations Catalyzed by Cytochrome P–450," Biochem. Biophys. Res. Commun., (1977) 76:541–9.

Jones, J. et al., "Predicting The Rates And Regioselectivity of Reactions Mediated By The P450 Superfamily" Methods in Enzymology, (1996) 272:326–35.

Jones, J. P., et al., "The Separation of the Intramolecular Isotope Effect for the Cytochrome P–450 Catalyzed Hydroxylation of n–Octane into Its Primary and Secondary Components," J. Am. Chem. Soc., (1987) 109(7):2171–3.

Jones, J.P., et al., "Stereospecific Activation of the Procarcinogen Benzo[a]pyrene: A Probe or the Active Sites o the C tochrome P450 Su er amil," Biochemistry, (1995)34:6956–61.

Jones, J.P., et al., "The Binding and Regioselecvitity of Reaction of (R)–and (S)–Nicotine with Cytochrome P–450cam: Parallel Experimental and Theoretical Studies," J. Am. Chem. Soc., (1993) 115:381–7.

Jones, J.P., et al., Accelerated Communication: Three Dimensional Quantitative Structure–Activity Relationship for Inhibitors of Cytochrome P4502C9,(1996) Drug Metab. Dispos., 24(1):1–6.

Karki, S.B., et al., "On Mechanism of Amine Oxidations by P450," Xenobiotica, (1995), 25(7):711–24.

Karki, S.B., et al., "Mechanism of Oxidative Amine Dealkylation of Substituted N,N–Dimethylanilines by Cytochrome P–450: Application of isotope Effect Profiles," J. Am. Chem. Soc., (1995) 117(13):3657–64.

Kim, S.S.; et al., "Comparative Hammett Studies of Imidoyl, Benzylic, Aldehydic Hydrogens Transfer and Related Reaction by t–Butoxyl Radical," Tetrahedron Lett., (1985) 26(7): 891–4.

Kobayashi, Y., et al., "Probing the Active Site of Cytochrome P450 2B1: Metabolism of 7–Alkoxycoumarins by the Wild Type and Five Site–Directed Mutants," Biochemistry, (1998) 37(19):6679–88.

Korzekwa, K. R., et al., "Theoretical Studies on Cytochrome P–450 Mediated Hydroxylation: A Predictive Model for Hydrogen Atom Abstraction," J. Am. Chem. Soc., (1990) 112:7042–6.

Korzekwa, K., et al., "The Use of Brauman's Least Squares Approach for the Quantification of Deuterated Chlorophenols," Biomed. & Environ. Mass Spectrom., (1990) 19:211–7.

Korzekwa, K.R., et al., "Predicting the Cytochrome P450 Mediated Metabolism of Xenobiotics," Pharmacogenetics, (1993) 3:1–18.

Lindsay Smith, J.R., et al., "Model Systems for Cytochrome P450 Dependent Mono–Oxygenases. Part 2. $_{1,2}$Kinetic Isotope Effects of the Oxidative Demethylation of Anisole and Me?H3JAnisole by Cytochrome P450 Dependent Mono–Oxygenases and Model Systems," J. Chem. Soc. Perkin Trans. II, (1983) 5:621–8.

Macdonald, T. L., et al., "Oxidation of Substituted N,N–Dimethylanilines by Cytochrome P–450: Estimation of the Effective Oxidation–Reduction Potential of Cytochrome P–450," (1989) Biochemistry, 28:2071–7.

Manchester, J.I., et al., "A New Mechanistic Probe for Cytochrome P450: An Application of Isotope Effect Profiles," J. Am. Chem. Soc., (1997) 119:5069–70.

Nelson, D.R., et al., P450 Superfamily: Update on New Sequences, Gene Mapping, Accession Numbers and Nomenclature, Pharmacogenetics, (1996) 6:1–42.

Northrop, D.B., "Deuterium and Tritium Kinetic Isotope Effects on Initial Rates," Methods Enzymol., (1982) 87:607–25.

Northrop, D.B., "Steady–State Analysis of Kinetic Isotope Effects in Enzymic Reactions," Biochemistry, (1975) 14(12)2644–51.

Omura, T., et al., "The Carbon Monoxide–Binding Pigment of Liver Microsomes," J. Biol. Chem., (1964) 239(7):2370–8.

Poulos, T. L., et al., "High–Resolution Crystal Structure of CytochromeP450cam," J. Mol. Biol., (1987) 195:687–700.

Ravichandran, K. G., et al., "Crystal Structure of Hemoprotein Domain of P450BM–3, a Prototype for Microsomal P450's," Science, (1993) 261:731–6.

Sakurai, H., et al., "Polar and Solvent Effects on Homolytic Abstraction of Benzylic Hydrogen of Substituted Toluenes by t–Butoxy Radical," J. Am. Chem. Soc., (1967) 89(2):458–60.

Shimoji, M., et al., "Design of a Novel P450: A Fucntional Bacterial—Human Cytochrome P450 Chimera," Biochemistry, (1998) 37:8848–52.

Silver, E.H., et al., "Structural Considerations in the Metabolism of Nitriles to Cyanide In Vivo," Drug Metab. Dispos., (1982) 10(5):495–8.

Smith, P. B., et al., "4–Ipomeanol and 2 Aminoanthracene Cytotoxicity in C3H/10T1/2 Cells Expressing Rabbit Cytochrome P450 4B1," Biochem. Pharmacol., (1995) 50(10):1567–75.

Szklarz, G. D., et al., "Site–Directed Nlutagenesis as a Tool for Molecular Modeling of Cytochrome P450 2B1," Biochemistry, (1995) 34:14312–22.

Tassaneeyakul, W., et al., "Human Cytochrome P450 Isoform Specificity in the Regioselective Metabolism of Toluene and o–, m– and p Xylene,"J. Pharmacol. Exp. Ther., (1996) 276(1):101–8.

Tyson, C. A., et al., "The Roles of Putidaredoxin and P450cam in Methylene Hydroxylation," J. Biol. Chem., (1972) 247 (18):5777–84.

Watanabe, Y., et al., "Kinetic Study on Enzymatic S–Oxygenation Promoted by a Reconstituted System with Purified Cytochrome P–450," Tetrahedron Lett., (1980) 21:3685–8.

Westheimer, F. H., "The Magnitude of the Primary Kinetic Isotope Effect for Compounds of Hydrogen and Deuterium," Chem. Rev., (1961) 61(3):265–73.

White, R. E., et al., "Oxygen Activation by Cytochrome P–450," Ann. Rev. of Biochem., (1980) 49:315–56.

White, R.E., et al., "Active Site Mechanics of Liver Microsomal Cytochrome P–450, " Arch. Biochem. Biophys., (1986) 246(1):19–32.

White, R.E., et al., "Stereochemical Dynamics of Aliphatic Hydroxylation by Cytochrome P–450,"J. Am. Chem. Soc., (1986) 108: 6024–31.

Wislocki, P.G., et al., "Reactions Catalyzed by the Cytochrome P–450 System," Enzymatic Basis of Detoxication, (1980) 1:135–82.

Yin, H., et al., "*Designing Safer Chemicals: Predicting the Rates of Metabolism of Halogenated Alkanes,*" Proc. Natl. Acad. Sci. USA, (1995) 92(24):11076–80.

Zerner, Michael C., "*Semiempirical Molecular Orbital Methods,*" Reviews in Computational Chemistry II, Chapter 8, 313–365 (1991). VCH Publishers, Inc. NY.

International Search Report for PCT/US99/17713 dated Nov. 11, 1999.

Abstract No. XP–002122407, P84 to Johnson et al., "Automated Modeling Predicts Active Site Geometrics Consistent with the Regiospecificity of P450s 2C3v and 2C5 for Progesterone Hydroxylation," FASEB Journal 11(9):P785 (1997).

Gillette et al., "Overview: Theoretical Aspects of Isotope Effects on the Pattern of Metabolites Formed by Cytochrome P–450," Biological Reactive Intermediates IV, Witmer et al., Eds. Plenum Press, NY (1990), pp. 87–94.

Korzekwa et al., "Theory for the Observed Isotope Effects from Enzymatic Systems that Form Multiple Products via Branched Reaction Pathways: Cytochrome P–450," Biochemistry 28:(23), pp. 9012–9018. (1989).

Abstract No. XP–000578888, Geladi et al., "Partial Least-Squares Regression: A Tutorial," Analytica Chimica Acta, 185 (1986) 1–17.

REACTION A (410)

REACTION B (403)

$$\frac{V_{(A)}}{V_{(B)}} = \frac{\frac{K_{34(A)}}{K_{34(B)}} + \frac{K_{34(A)}}{K_{35(B)}}}{1 + \frac{K_{34(A)}}{K_{34(B)}}}$$

405

| LOVASTATIN Regioselectivity/Output Table | | |
|---|---|---|
| site # | Ea | Lability Bin |
| 1 | 6.71 | labile |
| 2 | 7.129 | labile |
| 3 | 8.944 | moderate |
| 4 | 9.502 | moderate |
| 5 | 9.806 | moderate |
| 6 | 10.396 | moderate |
| 7 | 10.515 | stable |
| 8 | 10.715 | stable |
| 9 | 10.856 | stable |
| 10 | 10.995 | stable |
| 11 | 11.02 | stable |
| 12 | 11.061 | stable |
| 13 | 11.097 | stable |
| 14 | 11.375 | stable |
| 15 | 11.401 | stable |
| 16 | 11.583 | stable |
| 17 | 11.599 | stable |
| 18 | 11.599 | stable |
| water | 10 | NA |

RELATIVE RATES OF CYTOCHROME P450 METABOLISM

CROSS-REFERENCE TO RELATED APPLICATIONS

This patent application is a continuation-in-part of U.S. patent application Ser. No. 09/368,511, filed Aug. 5, 1999, naming Korzekwa et al. as inventors and titled "Use of Computational and Experimental Data to Model Organic Compound Reactivity in Cytochrome p450 Mediated Reactions and to Optimize the Design of Pharmaceuticals" which claims the benefit of U.S. Provisional Patent Application No. 60/095,460 filed Aug. 5, 1998, titled "Use of Computational and Experimental Data to Model Organic Compound Reactivity in Cytochrome p450 Mediated Reactions and to Optimize the Design of Pharmaceuticals." It is also related to U.S. Provisional Patent Application Patent Application No. 60/217,227 titled "Accessibility Correction Factors for Quantum Mechanical and Molecular Models of Cytochrome p450 Metabolism." Each of these patent applications, except Provisional Patent Application No. 60/095,460, as well as any other patents, patent applications and publications cited herein, are herein incorporated by reference in their entirety for all purposes.

The U.S. Government may have certain rights in this invention pursuant to NIH Grant No. 091122.

FIELD OF THE INVENTION

The present invention relates generally to systems and methods for analyzing the reactive sites of substrates, in particular drugs. More specifically, the invention relates to systems and methods for determining the relative metabolic reaction rates of these reactive sites, especially with respect to alternative reaction pathways in the cytochrome p450 enzymes, so as to model and predict the metabolic properties of the substrate, as well as to design and redesign such substrates in order to achieve desired metabolic properties.

BACKGROUND OF THE INVENTION

Drug development is an extremely expensive and lengthy process. The cost of bringing a single drug to market is about $500 million to $1 billion dollars, with the development time being about 8 to 15 years. Drug development typically involves the identification of 1000 to 100,000 candidate compounds distributed across several compound classes that eventually lead, to a single or several marketable drugs.

Those thousands of candidate compounds are screened against biochemical targets to assess whether they have the pharmacological properties that the researchers are seeking. This screening process leads to a much smaller number of "hits" (perhaps 500 or 1000) which display some amount of the desired properties, which are narrowed to even fewer "leads" (perhaps 50 or 100) which are more efficacious. At this point, typically, the lead compounds are assayed for their ADME/PK (absorption, distribution, metabolism, elimination/pharmokinetic) properties. They are tested using biochemical assays such as Human Serum Albumin binding, chemical assays such as pKA and solubility testing, and in vitro biological assays such as metabolism by endoplasmic reticulum fractions of human liver, in order to estimate their actual in vivo ADME/PK properties. Most of these compounds are discarded because of unacceptable ADME/PK properties.

In addition, even optimized leads that have passed these tests and are submitted for FDA clinical trials as investigational new drugs (INDs) will sometimes show undesirable ADME/PK properties when actually tested in animals and humans. Abandonment or redesign of optimized leads at this stage is extremely costly, since FDA trials require formulation, manufacturing and extensive testing of the compounds.

The development of compounds with unacceptable ADME/PK properties thus contributes greatly to the overall cost of drug development. If there was a process by which compounds could be discarded or redesigned at an earlier stage of development (the earlier the better), then great savings in terms of money and time could be achieved. The current art essentially offers no comprehensive method by which this can be done.

A large portion of all drug metabolism in humans and most all organisms is carried out by the cytochrome p450 enzymes. The cytochrome p450 enzymes (CYP) are a superfamily of heme-containing enzymes that include more than 700 individual isozymes that exist in plant, bacterial and animal species. Nelson et al. *Pharmacogenetics* 1996 6, 1–42. They are monooxygenase enzymes. Wislocki et al., in *Enzymatic Basis of Detoxification* (Jakoby, Ed.), 135–83, Academic Press, New York, 1980. Although humans share the same several CYP isozymes, these isozymes can vary slightly between individuals (alleles) and the isozyme profile of individuals, in terms of the amount of each isozyme that is present, also varies to some degree.

It is estimated that in humans, 50% of all drugs are metabolized partly by the p450 enzymes, and 30% of drugs are metabolized primarily by these enzymes. The most important CYP enzymes in drug metabolism are the CYP3A4, CYP2D6 and CYP2C9 isozymes. While modeling techniques do exist for predicting substrate metabolism by enzymes other than CYP, no sufficiently accurate technique exists for modeling metabolism by the CYP enzymes. To the extent that modeling techniques are available for other enzymes, they work by analyzing the either the interactions between enzyme and substrate, or the common characteristics for a series of substrates. See, for example, Schramm, "Enzymatic transition states and transition state analog design." *Annu Rev Biochem* 1998; 67: 693–720; Hunter, "A structure-based approach to drug discovery; crystallography and implications for the development of antiparasite drugs." *Parasitology* 1997; 114 Suppl: S17–29; Gschwend et al, "Molecular docking towards drug discovery." *Mol Recognit* 1996 Mar–Apr; 9(2): 175–86.

While these modeling techniques are partially effective for some enzymes, they can be ineffective for the CYP enzymes. This is because the CYP enzymes do not have binding specificities in the way that other enzymes do. CYP3A is almost completely nonspecific from a steric perspective, while CYP2D6 and CYP2C9 are only modestly sterically specific. Gross steric and electrostatic properties of a substrate have a secondary effect on their metabolism by the CYP enzymes, at most. Thus modeling techniques in the current art cannot be used to model CYP enzyme metabolism.

In view of the foregoing importance of the CYP enzymes to drug metabolism, a modeling technique for CYP-substrate interaction and metabolism would be highly beneficial. Such a technique would provide researchers with valuable ADME/PK information on compounds at an early stage in the development process.

SUMMARY OF THE INVENTION

The present invention addresses this need by providing methods and systems for identifying reactive sites on a substrate molecule, typically a drug, and determining the relative rates of metabolism of those reactive sites by the CYP enzymes. Determining these relative rates is an important factor in determining the absolute rate of metabolism of the individual sites and the substrate molecule as a whole. This information is also a critical factor in determining whether and how the substrate can be redesigned to improve its ADME/PK properties. In this regard, it is particularly important to know how the relative rates compare to the rate of a non-metabolic side reaction (branch pathway) such as water generation and regeneration of the substrate. The systems and method described there can be used in conjunction with the present invention to provide even more comprehensive information on CYP substrate metabolism.

In a preferred embodiment of the invention, one or more substrate molecule compounds (drugs), or one or more classes of such molecule compounds are presented in a standard representation system such as an organic chemistry string of atoms, a two-dimensional structure, a UIPAC standard name, a 3D coordinate map, or any other commonly used representation. If not already in 3D format, the molecules are converted to 3D format using a 3D formatting software tool such as Corina or Concord and then optimized using AM1.

For each molecule, the reactive sites are identified. The reactive sites are then converted to a radical species to predict their activation energies and reaction rates with respect to the last step of the CYP catalytic cycle. The reaction rate for each reactive site is then compared to the reaction rate for the alternate branch of water decoupling, to determine whether the reactive site is labile, moderately labile or stabile compared to water decoupling. The water decoupling reaction rate is determined by isotope effect information. The molecule as a whole is then characterized in terms of the "relative reaction rates" or "relative rates" for these reactive sites. This information is used to determine whether the molecule has the proper ADME/PK properties, whether it can be redesigned to achieve the most desired ADME/PK properties, and which sites should be modified in order to do this. This information can also be used in conjunction with information obtained about other steps in the CYP catalytic cycle.

One aspect of the invention pertains to methods for predicting an effect of a molecular modification on the metabolism rate of the molecule, the method including the operations of predicting or determining a reaction rate at a first site on the molecule, comparing the reaction rate to that of a branch pathway, and characterizing that site based upon this reaction rate. This allows one to model and predict the effect of the molecular modification on the metabolism of the molecule. The molecule is typically metabolized by a CYP enzyme and the branch pathway is typically a water decoupling reaction. The method can be and is typically repeated for multiple sites on a molecule.

These sites or reactive sites are binned into categories based upon their relative reaction rates with respect to the branch pathway, such as labile for sites that react faster than water decoupling, moderately labile for sites that react at about the same rate as water decoupling, and stable for sites that react slower than water decoupling. The water decoupling activation energy and reaction rate is determined through isotope effect unmasking. The reaction rate of an reactive site is typically determined from its radicalized intermediate form, e.g., by hydrogen abstraction for aliphatic carbon reactive sites and methoxy radical addition for aromatic carbon reactive sites.

Another aspect of the invention pertains to methods for characterizing the reactive site of a substrate molecule, the method including the operations of determining an activation energy for the reactive site, calculating a rate constant for the reactive site based upon its activation energy, and comparing the activation energy or rate constant to a branch pathway associated with the enzyme-substrate complex. The substrate is typically metabolized by a CYP enzyme and the branch pathway is typically a water decoupling reaction. The method can be and is typically repeated for multiple sites on a substrate.

These sites or reactive sites are binned into categories based upon their relative reaction rates with respect to the branch pathway, such as labile for sites that react faster than water decoupling, moderately labile for sites that react at about the same rate as water decoupling, and stable for sites that react slower than water decoupling. The water decoupling activation energy and reaction rate is determined through isotope effect unmasking. The reaction rate of an reactive site is typically determined from its radicalized intermediate form, e.g., by hydrogen abstraction for aliphatic carbon reactive sites and methoxy radical addition for aromatic carbon reactive sites.

Another aspect of the invention pertains to methods for predicting an effect of a molecular modification on the metabolism rate of the molecule, the method including the operations of predicting or determining a reaction rate at a first site on the molecule, comparing the reaction rate to that of a branch pathway, and characterizing that site based upon this reaction rate. This allows one to model and predict the effect of the molecular modification on the metabolism of the molecule. The molecule is typically metabolized by a CYP enzyme and the branch pathway is typically a water decoupling reaction. The method can be and is typically repeated for multiple sites on a molecule.

Another aspect of the invention pertains to computer systems for implementing the methods described above. Another aspect of the invention pertains to computer-program products including a machine-readable medium on which is provided program instructions for implementing one or more of the computer systems or methods described above. Any of the computer system user interfaces or methods of the invention may be represented as program instructions that can be provided on such computer-readable media.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Figure 1:
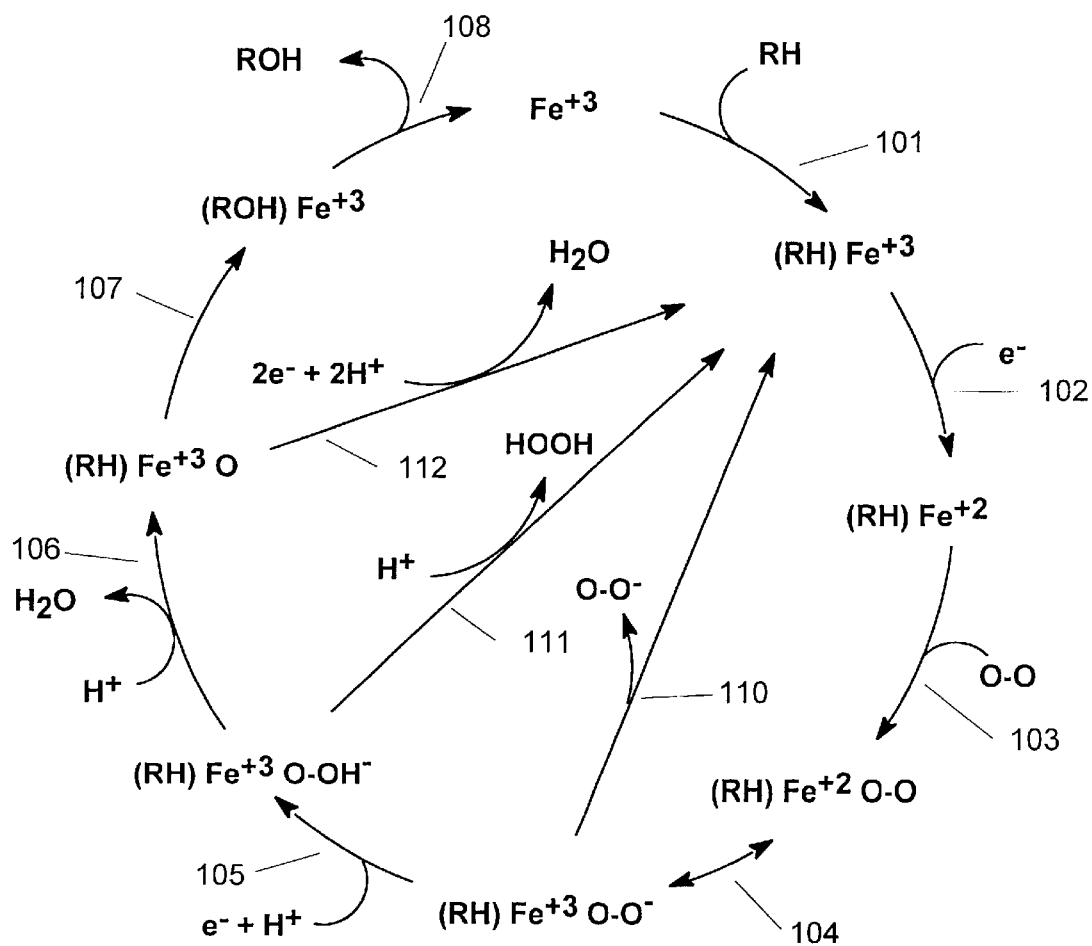
FIG. 1 is a schematic illustration of the mammalian cyctochrome p450 catalytic cycle, including the non-metabolic decoupling reactions.

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well known processes, procedures and components have not been described in detail so as not to unnecessarily obscure aspects of the present invention.

A "molecular modification" as referred to herein refers to any change in the chemical feature of a molecule. Molecular modifications include any change in a molecule in any step of its metabolic process. A drug that is being catalyzed by a CYP enzyme will typically undergo several molecular modifications through its metabolic cycle.

A "metabolic enzyme" as referred to herein refers to any enzyme that is involved in xenobiotic metabolism. Many metabolic enzymes are involved in the metabolism of exogenous compounds. Metabolic enzymes include enzymes that metabolize drugs, such as the CYP enzymes, uridine-diphosphate glucuronic acid glucuronyl transferases and glutathione transferases.

"Xenobiotic metabolism" as referred to herein refers to any and all metabolism of foreign molecules that occurs in living organisms, including anabolic and catabolic metabolism.

A "reactive site" as referred to herein refers to a site on a substrate molecule that is susceptible to metabolism and/or catalysis by an enzyme. It is to be distinguished from a "active site," which is the region of an enzyme that is involved in catalysis.

"Reaction rate" as referred to herein refers to the kinetic rate of a chemical reaction or a single step of a chemical reaction. The reaction rate can be predicted by modeling the transition state or estimating the activation energy from the difference in free energy between a substrate and an intermediate form. The term "reaction velocity" is used interchangeably with "reaction rate."

"Metabolism rate" as referred to herein refers to the overall rate of metabolism of a substrate, regardless of which reactive sites are involved in the metabolism of the drug to a non-reactive form. Thus the reaction rates of all of the reactive sites are involved in determining the metabolic rate.

A "complex" as referred to herein is an enzyme-substrate complex formed by covalent and other bonds that may or may not lead to metabolism of the substrate/drug.

A "main pathway" as referred to herein refers to any chemical reaction, but more typically a reaction of particular interest. A main pathway may have a "branch pathway" that is an alternate reaction to the main pathway. The branch pathway typically yields a different product or product than the reaction that is being referred to. Branch pathways can include "decoupling reactions" which are non-metabolic reaction steps. The CYP catalytic cycle, which will be discussed in more detail below, has three decoupling reactions, one decoupling to superoxide, one decoupling to hydrogen peroxide, and one decoupling to water.

A "catalytic cycle" as referred to herein is a series of substrate reaction steps that are catalyzed by an enzyme, such as the CYP catalytic cycle.

An "intramolecular intrinsic isotope effect" as referred to herein is an observed effect of a reactive chemical group with different isotopes that non-preferentially react with an enzyme except for the effect of their differing isotopes. An intermolecular isotope effect will typically be expressed as the non-unitary ratio of two rate constants for two isotopes. An "intermolecular isotope effect," on the other hand, is masked when the rate-limiting step precedes the isotopically sensitive step. However, the isotope effect will be "unmasked" to varying degrees, up to the ratio of the "intramolecular intrinsic isotope effect," if a branched pathway is in competition with the isotopically sensitive step. The degree of unmasking depends on the ratio of the rate constant of a branch pathway to the main pathway.

"Accessibility" as referred to herein is the degree to which steric and orientation characteristics of a molecule affect its rate of metabolism and activation energy. "Accessibility correction factors" are factors that quantify these characteristics.

FIG. 1 illustrates the oxidative hydroxylation catalytic cycle for the mammalian CYP enzyme. The top of the figure shows a generic starting substrate (RH) and generic product (ROH). This hydroxylation reaction is often the first step in metabolizing an exogenous compound, and partly explains the importance of the CYP enzymes in drug deactivation/metabolism.

A first step 1 of the catalytic cycle, 101, shows the initial binding of the substrate to the heme iron atom of the enzyme, which changes the equilibrium spin state of the heme iron from low to high. This lowers the reduction potential of the iron, thus facilitating transfer of an electron from NADPH, via cytochrome p450 reductase, to the iron atom in a second step 2, 102. In a third step 3, 103, molecular oxygen binds to the iron atom. In a fourth step 4, 104, the iron is reduced by one electron and the iron is oxidized from a ferrous state to a ferric state. At this point, the oxygen can be decoupled from the enzyme as superoxide in a non-metabolic reaction, thus taking the enzyme-substrate complex back to its initial state in a tenth step 10, 110. Otherwise, the oxygen is reduced by one more electron in a fifth step 5, 105, thus forming a peroxy intermediate with the enzyme-substrate complex. Here, a hydrogen peroxide decoupling reaction can take place, an eleventh step 11, 111, which takes the enzyme-substrate complex back to the initial state.

Otherwise, in a sixth step 6, 106, the peroxide undergoes heterolytic cleavage, with one oxygen leaving the complex as a water molecule and the other oxygen coordinating with the iron atom as a reactive oxygen atom. A water decoupling reaction, a twelfth step 12, 112, can take the enzyme-substrate complex back to the initial state. Otherwise, the reactive oxygen is transferred to the substrate to form an oxidized product, a seventh step 7, 107. The product, then dissociates from the enzyme, an eighth step 8, 108.

Note that the peroxide decoupling reaction, 111 and the water decoupling reaction, 112, both yield the substrate back in its original form in complex with the enzyme. These pathways thus reduce the rate of metabolism of the substrate. If either of the decoupling pathways predominate in the CYP catalytic cycle, then the substrate is unlikely to be metabolized rapidly.

Experimental evidence for the existence of these reaction pathways and intermediates is described in U.S. patent application Ser. No. 09/368,511, by Korzekwa et al. That patent application also contains additional material on the mechanisms of CYP enzyme-substrate interaction.

This evidence also shows that the last steps of the CYP catalytic cycle, steps 107 and 108, are not typically the rate-limiting steps in the sense that they are not the slowest steps in the catalytic cycle. They are often the "product-determining" steps, however. While rate-limiting steps are usually though of as the steps that determine that rate of product formation, if there is a non-metabolic alternate pathway that competes with a faster step, that'step can become the product-determining step. This scenario describes the CYP catalytic cycle. Because the last steps of the catalytic cycle compete with the water decoupling pathway 112, and because the water decoupling pathway has a significant reaction rate (see below), steps 107 and 108 are often the product-determining steps.

Therefore the relative rates analysis of the present invention, while it applies to these last steps in the catalytic cycle, does provide a useful, and often the most important, reaction rate information on substrate metabolism. To determine complete and absolute rates of substrate metabolism, at least some of the other reaction rates of in the CYP catalytic cycle should be measured. In a preferred embodiment, the model also accounts for either or both of the decoupling reactions 110 and 111. It appears that the peroxide decoupling step 111, for example, is somewhat substrate dependent. Therefore, the model may make use of certain substrate characteristics to predict the degree to which this decoupling reaction affects the absolute rate of metabolism.

Figure 2:
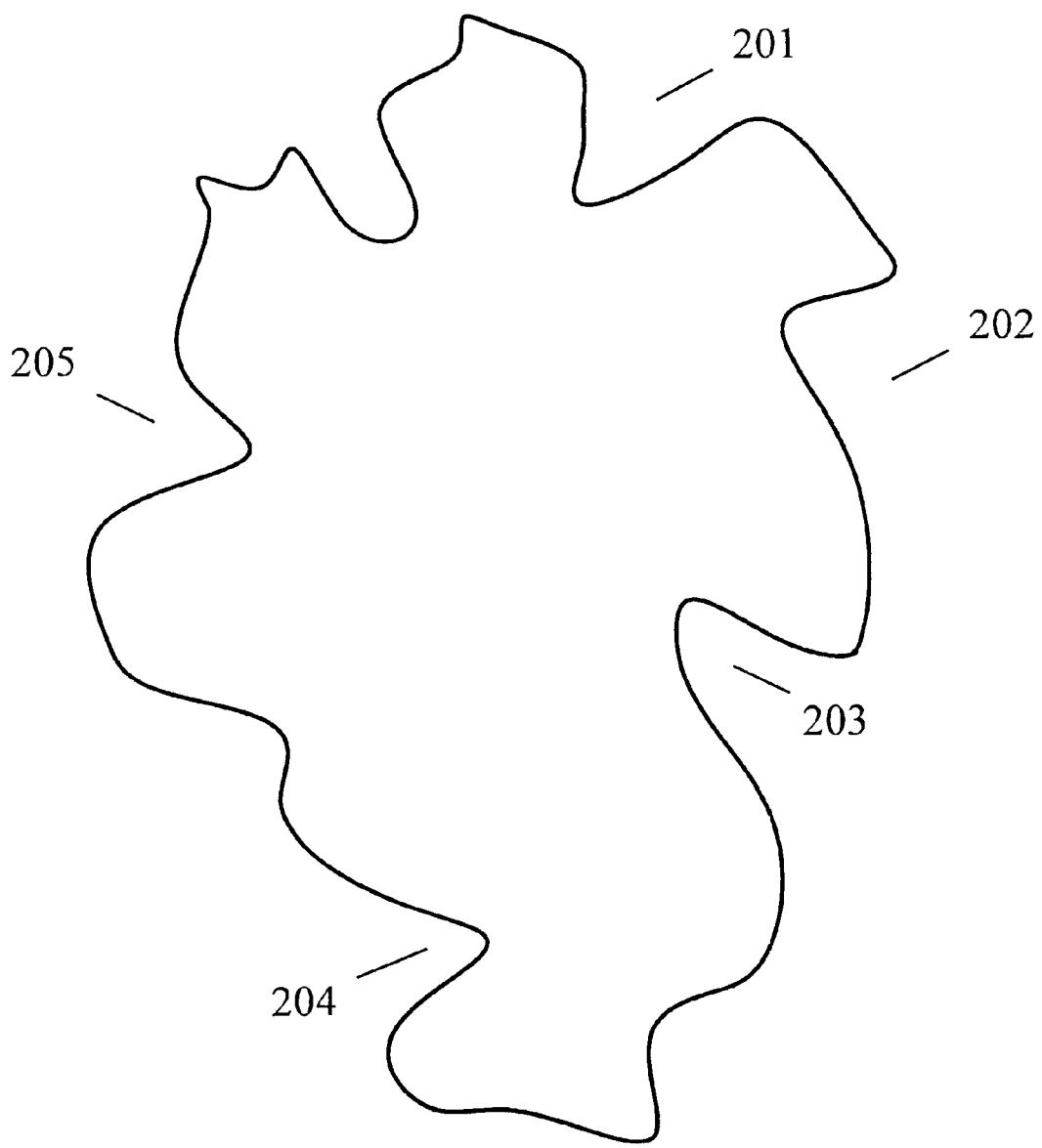
FIG. 2 is a schematic illustration of a substrate molecule (drug) with several reactive sites.

FIG. 2 is a simplified, schematic illustration of a substrate molecule with several reactive sites, 201–205, for CYP enzyme metabolism. One of the most common ADME/PK problems with a drug candidate is that it is metabolized too quickly. In many cases, an Fox ideal drug would be metabolized slowly enough so that it can be administered about once a day. In the current art, if a drug candidate was being metabolized too quickly for daily administration, the designers of the drug would try to redesign it, typically by modifying the most reactive site in a manner that would make it considerably more stable.

However, changing this most reactive site, even by making it extremely stable or even non-reactive, may or may not result in an appreciable decrease in the rate of metabolism of the drug. The result is essentially unpredictable by methods of the current art. A drug designer much less has the ability to predict how a more minor change in a reactive site will affect the metabolism of the drug. For instance, site 203 might be observed to be the most reactive site. A drug designer could then modify it to make more stable or even unreactive in an attempt to decrease the overall metabolic rate of the substrate. In some instances this will be successful, but if the substrate has one or more reactive sites that also have relatively high reactive rates, then these sites will often "take over" the metabolism of the substrate and the overall metabolic rate will remain essentially unchanged.

Therefore, a drug designer would have to go through the time-consuming process of redesigning one site as essentially a shot in the dark, re-testing the ADME/PK properties, and then redesigning that site and/or one or more of the other reactive sites as additional shots in the dark. After conducting this process on most or all of the reactive sites of the drug, the designer might find that it is essentially impossible to achieve the ADME/PK properties that are desired, particularly without reducing, or perhaps destroying, the desired pharmacological properties of the drug. The chances of altering the pharmocological properties of the drug greatly increase as more and more redesigns of the drug are carried out.

Slowing down the rate of metabolism of a drug candidate is by no means the only ADME/PK property that drug designers try to affect. They also may try to speed up the rate of metabolism of drug. In addition, it is generally preferable that a drug have more than one deactivating pathway and/or reactive site, so that chances of dangerous drug interaction, via blocking the primary metabolic pathway, are minimized. The CYP enzymes are also susceptible to induction, so that one drug may induce faster metabolism of another drug. The fact that multiple reactive sites are often desirable, for both these reasons, can make the design of the drug even more complicated.

Figure 3A:
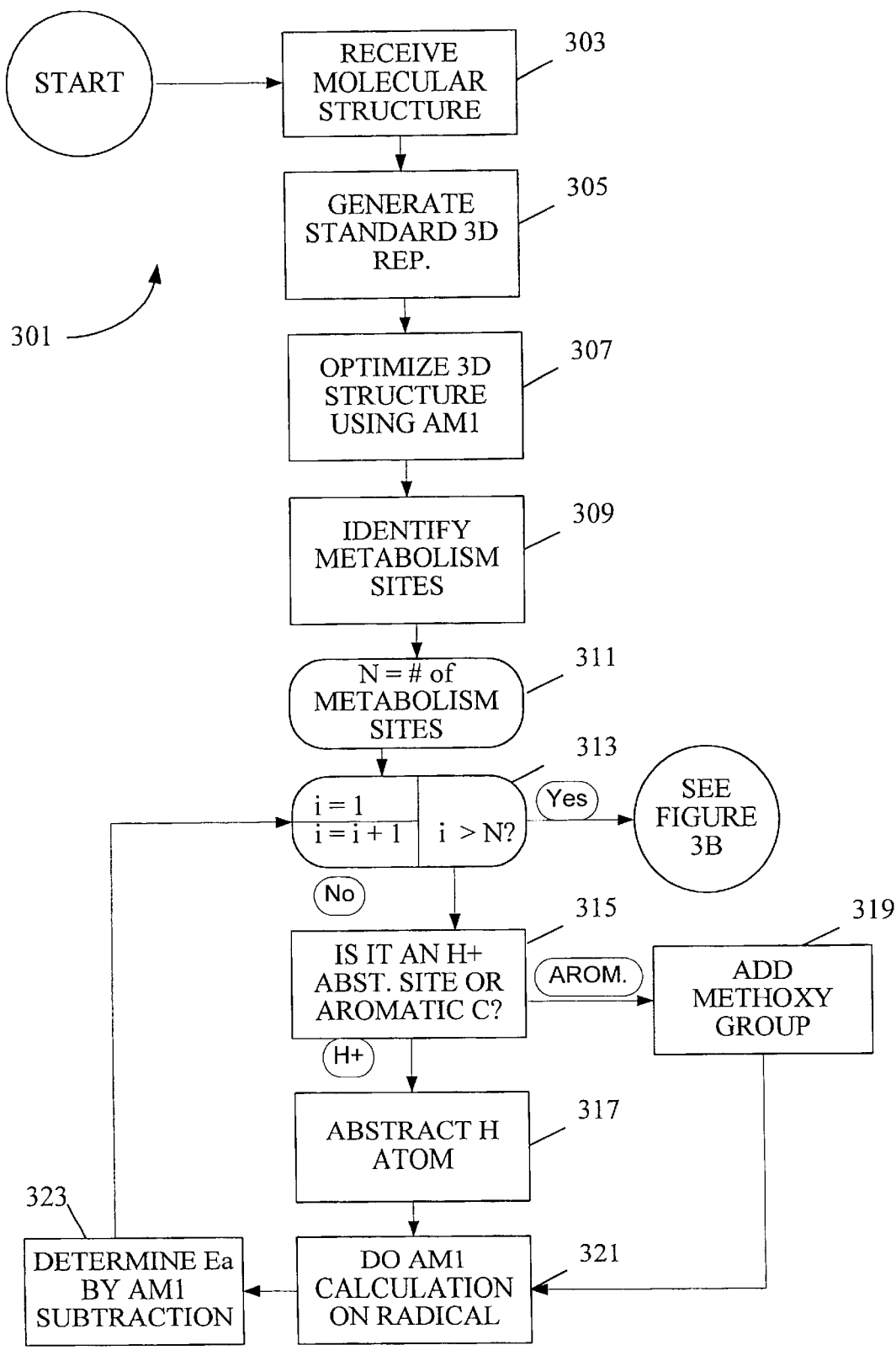
FIGS. 3A and 3B together make up a flowchart for determining the relative reaction rates of a substrate molecule, starting with the substrate's molecular structure.
Figure 3B:
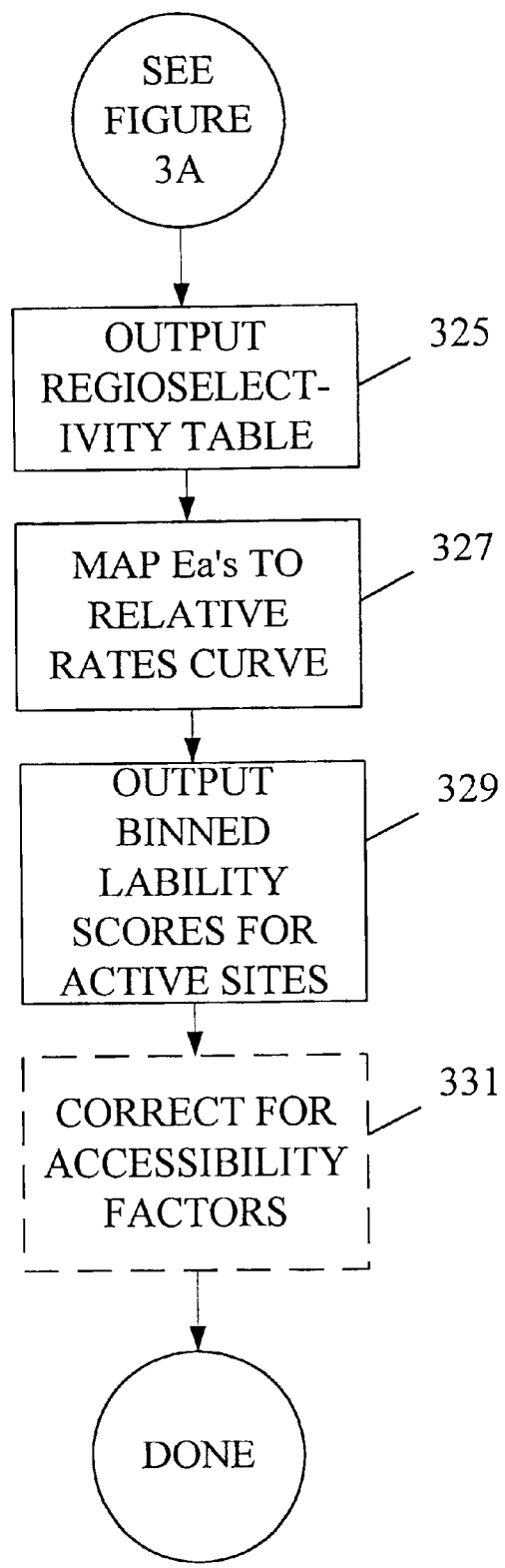

FIGS. 3A and 3B make up a flowchart which illustrates from a high-level one preferred process, 301, for generating the relative rates curve and associated information for a substrate molecule. Initially at operation 303, the molecular structure of the substrate is received. The molecular structure can be received as an organic chemistry string of atoms, a two-dimensional structure, a IUPAC standard name, a 3D coordinate map, or as any other commonly used representation. If not already in 3D form, a 3D coordinate map of the molecule is generated, using a geometry program such as Corina or Concord. See 303. The 3D structure generator Corina is available from Molecular Simulations, Inc., of San Diego, Calif. and Molecular Networks GmbH of Erlange, Germany. Concord is available from Tripos, Inc. of St. Louis, Mo. Corina uses straightforward rules about molecular bond and functional group conformation to generate an approximate geometry 3D structure, which is optimized to a local energy minimum. For instance, if an amine group is encountered, then it will be placed in a planar conformation, as that group normally exists. Concord applies a similar method, but also uses a limited set of molecular mechanical rules involving branch angles, strain and torsion, to achieve its 3D structure.

This approximate 3D geometry structure is then optimized with a more sophisticated modeling tool, typically AM1. AM1 is a semi-empirical quantum-chemical modeling program that optimizes the given 3D structure to that local energy minimum. See 307. It calculates electron density distributions from approximate molecular orbitals. It also calculates an enthalpy value for the molecule. AM1 is available as part of the public-domain software package MOPAC, which is available from the Quantum Chemistry Program Exchange, Department of Chemistry, Indiana University, Bloomington, Ind. The MOPAC-2000 version of MOPAC can be obtained from Schrödinger, Inc., of Portland, Oreg.

The process then identifies each reactive site of metabolism on the molecule. See 309. In the preferred embodiment, the reactive sites include aliphatic carbons and aromatic carbons. These sites are chosen because CYP enzymes generally oxidize the substrate molecules at these sites. Other reactive sites can be considered in other embodiments, depending on the enzyme and/or class of substrates under consideration. The process then analyzes each reactive site, beginning with operations 311 and 313, where the system sets a variable N equal to the number of reactive sites to be considered (311) and iterates over those sites (311). Iterative loop operation 313 initially sets an index value "i" equal to 1. It then determines whether the current value of i is greater than the value of N. If not, it performs various operations to determine the activation energy ($E_A$) at that site.

In operation 315, the process determines whether the reactive site is an aliphatic carbon or aromatic carbon site. If it is an aliphatic carbon site, the process will remove a hydrogen atom, in silico, from the site. See 317. The molecule in this state is an intermediate form of the molecule which can be used to approximate the transition state the molecule will go in the oxidation reaction of step 108. The process then does a new AM1 calculation on the intermediate molecule to determine its 3D map and enthalpy. See 321. Note that the base molecule's 3D map and enthalpy were calculated at 307. The process then determines the enthalpy difference between the intermediate and base form of the molecule. Assuming that delta S is close to zero, which is a good assumption for the conditions under which CYP oxidation takes place, the process yields a good approximation of the activation energy value ($E_A$) for the reactive site. Other properties of the radical, such as its ionization potential, can also be used in estimating the $E_A$. If the reactive site is an aromatic carbon, then the process will add a methoxy group to the molecule to form the intermediate-radical. See 319. The operations for doing a new AM1 calculation, 321, and determining the $E_A$, 323, are the same as they are for proton abstraction sites.

Figure 3C:
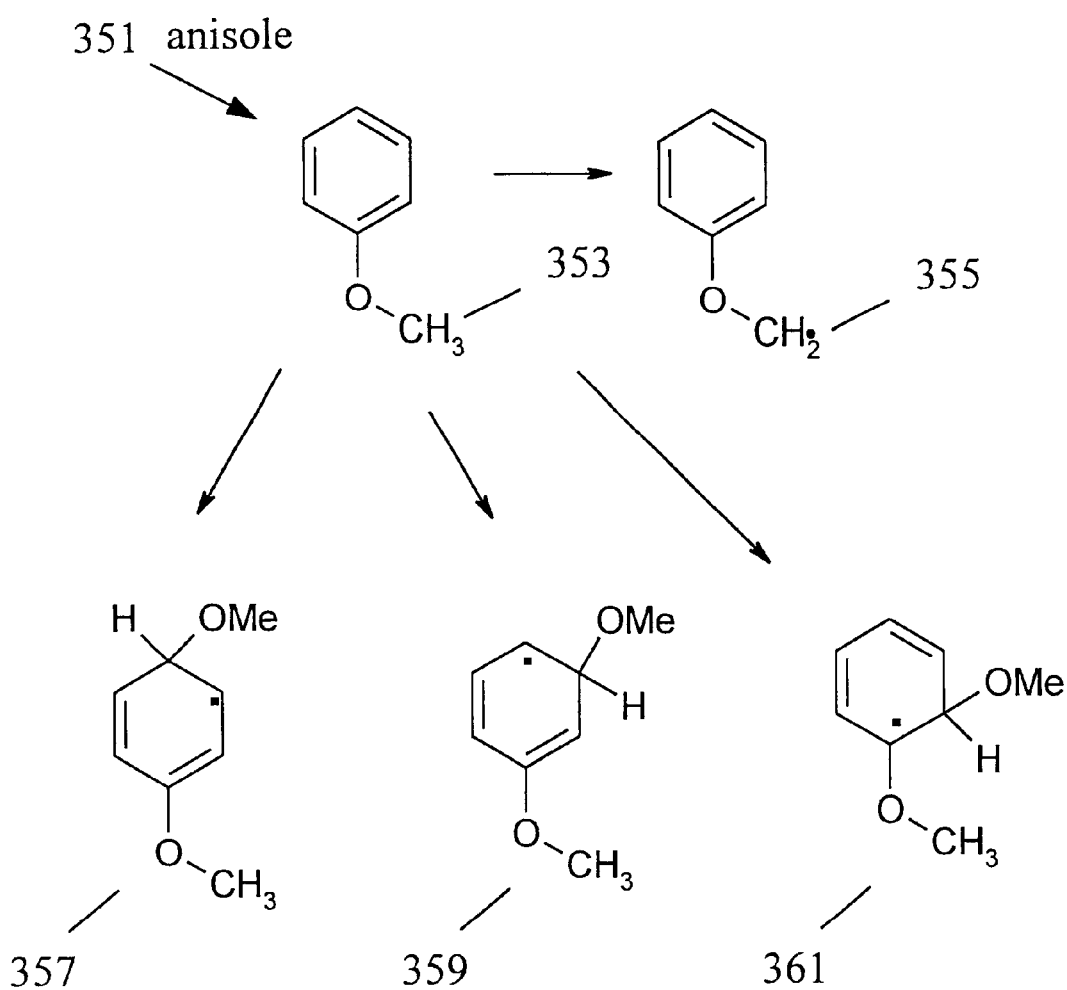
FIG. 3C shows an anisole molecule which has both an aliphatic and aromatic reactive sites.

FIG. 3C shows an anisole molecule, 351, which has both an aliphatic and aromatic reaction sites and can be used to illustrated both hydrogen abstraction and methoxy addition. The aliphatic reaction site of the anisole is the terminal methyl group 353. When a hydrogen ion (proton) is abstracted from this group, the intermediate that results has an extra electron on the reactive carbon. See 355. The aromatic ring can react in an ortho, meta or para fashion, with the methoxy group adding to those position as shown in intermediates 357, 359 and 361, respectively. The addition leaves a free electron on the ring.

Figures 5A, 5B:
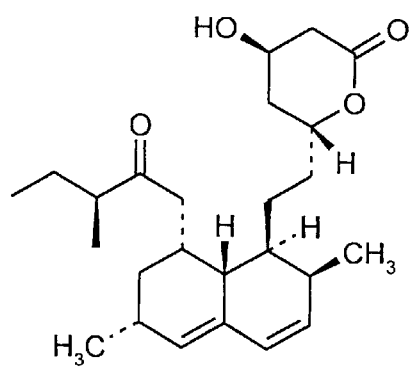
FIG. 5A is a schematic illustration of a regioselectivity table/sample output for an example substrate molecule, lovastatin. It includes the binning of reactive sites into the stabile, moderately stabile and labile categories as would be typical of the actual output.
FIG. 5B is an illustration of the substrate molecule lovastatin.
Figure 6:
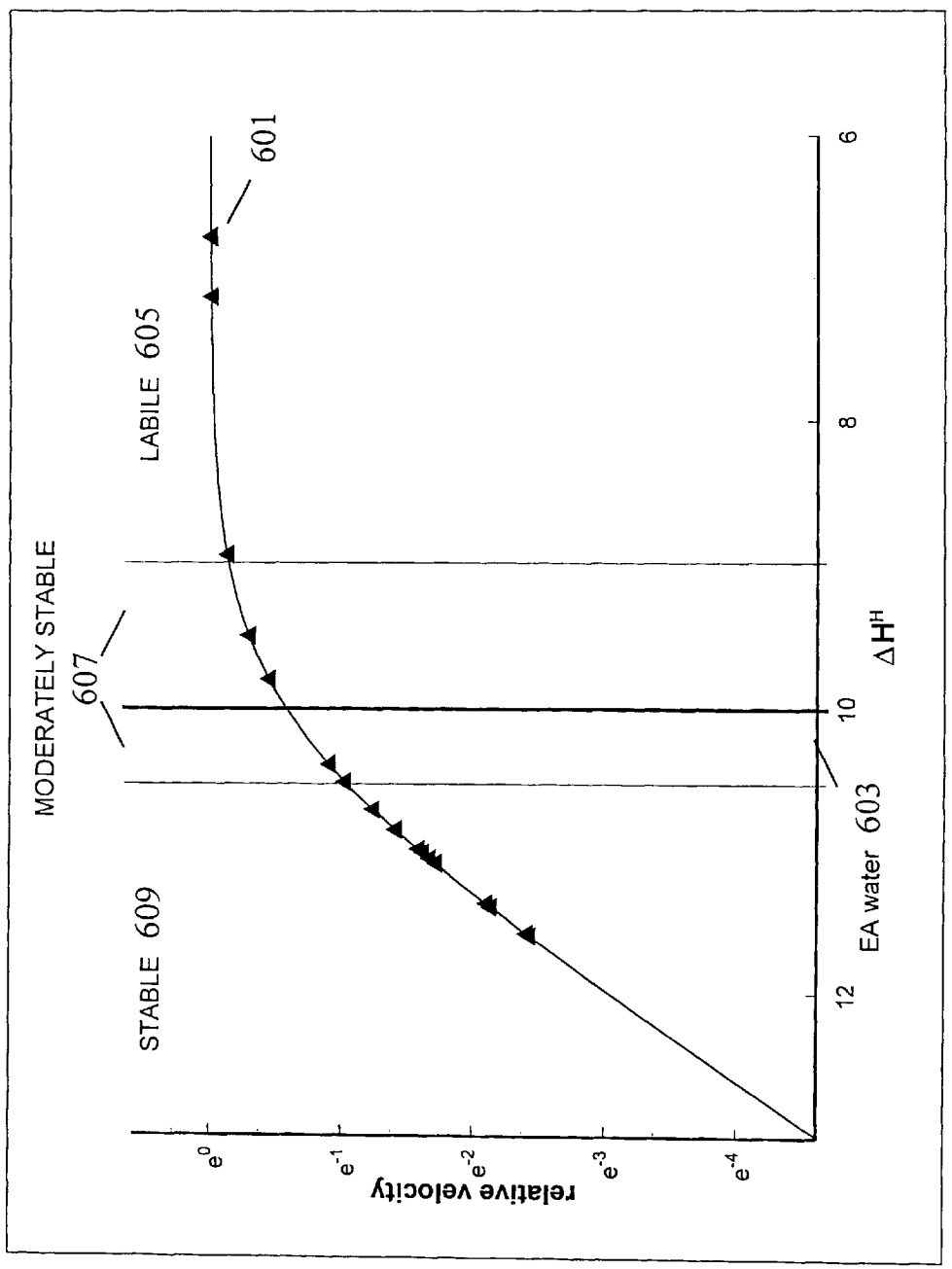
FIG. 6 is a schematic illustration of a relative rates curve plotted with the results from the regioselectivity table of FIG. 5A.

When i is greater than N, indicating that all the reactive sites have been analyzed, the process outputs a regioselectivity table or other arrangement of data that indicates the relative lability and activation energies of each of the reactive sites. See 325. A schematic example of such a regioselectively table is illustrated in FIG. 5A. The activation energies are used to map the reactive sites to a relative rates curve. See 327. A schematic example of such a relative rates curve is shown in FIG. 6. The reactive sites are then binned based upon their relative rates. See 329. The reactive sites are typically binned into three categories: labile, moderately labile and stabile. Details concerning the relative rates curve and activation energies of the reactive sites are discussed in the section below on "Method for Generating $K_W$."

For now, recognize that this concept of lability is typically specified with reference to a decoupling pathway in the enzyme's catalytic cycle. In the case of the CYP enzymes, the decoupling pathways are illustrated as steps 110, 11 and 112, which are the oxygen, hydrogen peroxide and water decoupling pathways. This is because these decoupling pathways regenerate the unreacted substrate. Substrate reactions with metabolic pathways that compete with, and proceed more rapidly than, these decoupling reactions provide for significantly faster metabolism. The relative rates data of the preferred embodiment specifically applies most directly to the last metabolic steps of the CYP catalytic cycle, steps 107 and 108, as they compare with the rate of water decoupling.

The final operation is an optional steric and orientation factor correction operation. See 331. As stated earlier, the CYP enzymes, particularly 3A4, are not sterically specific in the way that other enzymes are. However, in certain cases, a reactive site may be deeply buried within the substrate molecule, or the molecule may have a strongly preferred amphoteric orientation, so that the relative rate of the reactive site in metabolism is hindered or accelerated. In such cases, the user may wish to incorporate steric or orientation correction factors. Systems and method for incorporating such factors are discusses in U.S. Provisional Patent Application Patent Application No. 60/217,227, filed Jul. 10, 2000. However, this operation is optional, and in any case the main process of FIGS. 3A and 3B will yield useful information without operation 331.

In any case, it is worth noting that the core process for determining the relative rates is carried out without reference to the CYP enzymes or any other specific enzymes. As long as the enzymes being studied carry out metabolic by similar mechanisms, with the same transition states of the substrate being created, the data from one analysis of relative rates can usefully be applied to many enzymes.

Method for Generating $K_W$ (Alternate Branch Pathway Kinetics)

Figure 4:
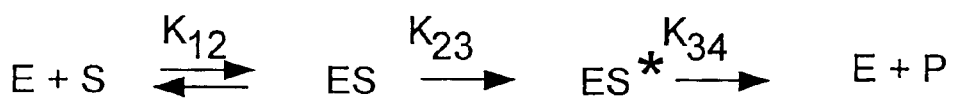
FIG. 4 shows sample reactions and a formula that illustrate the effect of branch pathways on reaction kinetics.
Figure 4:
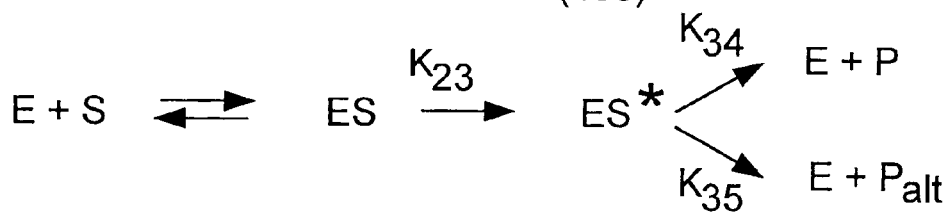

The importance of this water decoupling reaction in the kinetics and modeling of substrate metabolism will now be described. Kinetic studies have shown that the reduction steps 102 and 105 of the CYP catalytic cycle are the slowest steps of the cycle. Therefore, one would normally conclude that they are the "rate-limiting" steps with respect to product formation, and that other steps would not affect the overall reaction rate. FIG. 4 illustrates an example of this principle. Reaction A, 401, shows an enzyme (E) and substrate (S) forming an enzyme-substrate complex (ES) in step 12, an intermediate (ES*) in rate-limiting step 23, and an enzyme (E) and product (P) in the substrate oxidation step 34. In this typical example, increasing the rate of step 34 will of course not affect the overall rate of product-formation, since k34 (1)[ES*1]=k34(2)[ES*2]. In other words, the system with the larger rate constant k34(2) will have a lower concentration of the activated complex intermediate ES*. The net velocity of product formation remains the same.

However, if there is an alternate branch pathway k35 that forms an enzyme (E) and an alternate product ($P_{alt}$), as illustrated in reaction B, 403, then k34 can be the rate-limiting step for production of product P, if k34 is about equal to or less than k35. If k34 is greater than k35, then it contributes little or nothing to the overall rate of product formation. Equation 405 illustrates how the kinetic relationships in reaction 401 and 403 can be used to derive v(A)/v(B), which is the ratio of overall velocities of the two reactions. Note that if k35>>k34, then v(A)/v(B) approaches the ratio of k34(A)/k34(B).

In the CYP enzymes, one alternate branch pathway to product formation is the water decoupling reaction of step 112. If the rate of the product-formation step 108 is greater than the water decoupling reaction 112, then $k_W$ is not important and the catalytic cycle begins to resemble schematic reaction 401, where step 108 is not rate-limiting. If $k_W$ is comparable to or greater than $k_{34}$, then step 108 does becoming "product determining," and thus essentially determines the overall rate of the reaction.

Therefore, the $E_A$ and $k_W$ of the water decoupling reaction 112 is a critical reference point in characterizing the $E_A$'s of each of the reactive sites on a substrate. FIG. 5A is a schematic illustration of the regioselectivity table for the molecule lovastatin, which is used an example substrate to be analyzed. The molecule, which is illustrated in FIG. 5B, has 18 reactive sites. The table lists the $E_A$'s and relative reaction rates for each of the reactive sites of the substrate molecule. In a specific embodiment, the reactive sites include all hydrogen atom abstraction sites and all aromatic carbons.

The $E_A$ for water decoupling is shown for reference. Note that reactive sites 1–5 have activation energies lower than the activation energy for water decoupling. Positions 6–18 have activation energies that are greater than water decoupling. Note that at this point in this process, the reactive sites may not be binned into categories yet, so the regioselectivity table here may not have the third column as shown in FIG. 5A, which is actually the output table.

FIG. 6 is a schematic example of a relative reaction rates curve, where the lovastatin data from FIG. 5 is plotted. The $E_A$ of each reactive site is plotted as the X-axis independent variable. This $E_A$ represents the activation energy required to carry out the final product-formation step 108. Each $E_A$ yields a reaction rate for that step 108, which is used to calculate the Y-axis dependent variable. The point for each reactive site is marked as a triangle, 601. The Y-axis is the relative observed reaction velocity if the site represented on the X-axis is blocked. Sites that are not in competition with water formation have a value of 1, and sites competing with water formation have values less than 1. The relative velocities of the sites are plotted as the log of the ratio of the relative reaction rates. The reaction rate and activation energy for the water decoupling reaction 112 are plotted for reference, with the $E_A$ for water being 10 kcal/mole, 603. Methods for determining $k_W$ are described below.

The reactive sites are binned into three categories: labile, moderately labile and stable depending on their reaction rates/activation energies. The labile bin typically consists of reactive sites with $E_A$'s about 1.5 kcal/mole less than the $E_A$ for water and below. The moderately labile bin typically consists of reactive sites with $E_A$'s around $E_A$ water. The stable bin typically consists of reactive sites with $E_A$'s about 0.5 Kcal/mole above the $E_A$ water and above. These categories and their boundaries are somewhat arbitrary and are provided to assist a researcher in characterizing a candidate and developing a reengineering strategy, if necessary.

FIG. 6 illustrates that ten of the reactive sites are in the stabile category, and lie on the linear part of the curve where the log of relative velocity is inversely proportional to activation energy. Four of the reactive sites are in the moderately labile category, which is where the curve begins to change slope. Two of the reactive sites are in the labile category, which is in the plateau of the curve. Note that the overall metabolic rate of a substrate hardly differs if there are several reactive sites in this part of the curve or just one, because rendering one of these sites stable will still leave other labile sites. A substrate with several labile sites would typically be characterized as difficult to reengineer. After the relative rates curve is completed, a table is then output to the user, which includes the data for each reactive site and bins the reactive sites into the labile 605, moderately labile 607, and stable 609, categories, as illustrated in FIG. 5A.

Note again that the relative reaction rates for these reactive sites apply only to step 108, the last step of the CYP catalytic cycle. In many cases, this step is the primary determinant of the metabolic tendencies of the substrate because it determines the rate of product formation. In some cases, earlier steps, especially the steps involving peroxide cleavage and decoupling (steps 106 and 111), can be important contributors to the metabolic properties of the substrate. Information concerning these other steps can be combined with information from the present invention.

Indirect Determination of $k_W$ (The Isotope Effect)

Figure 7:
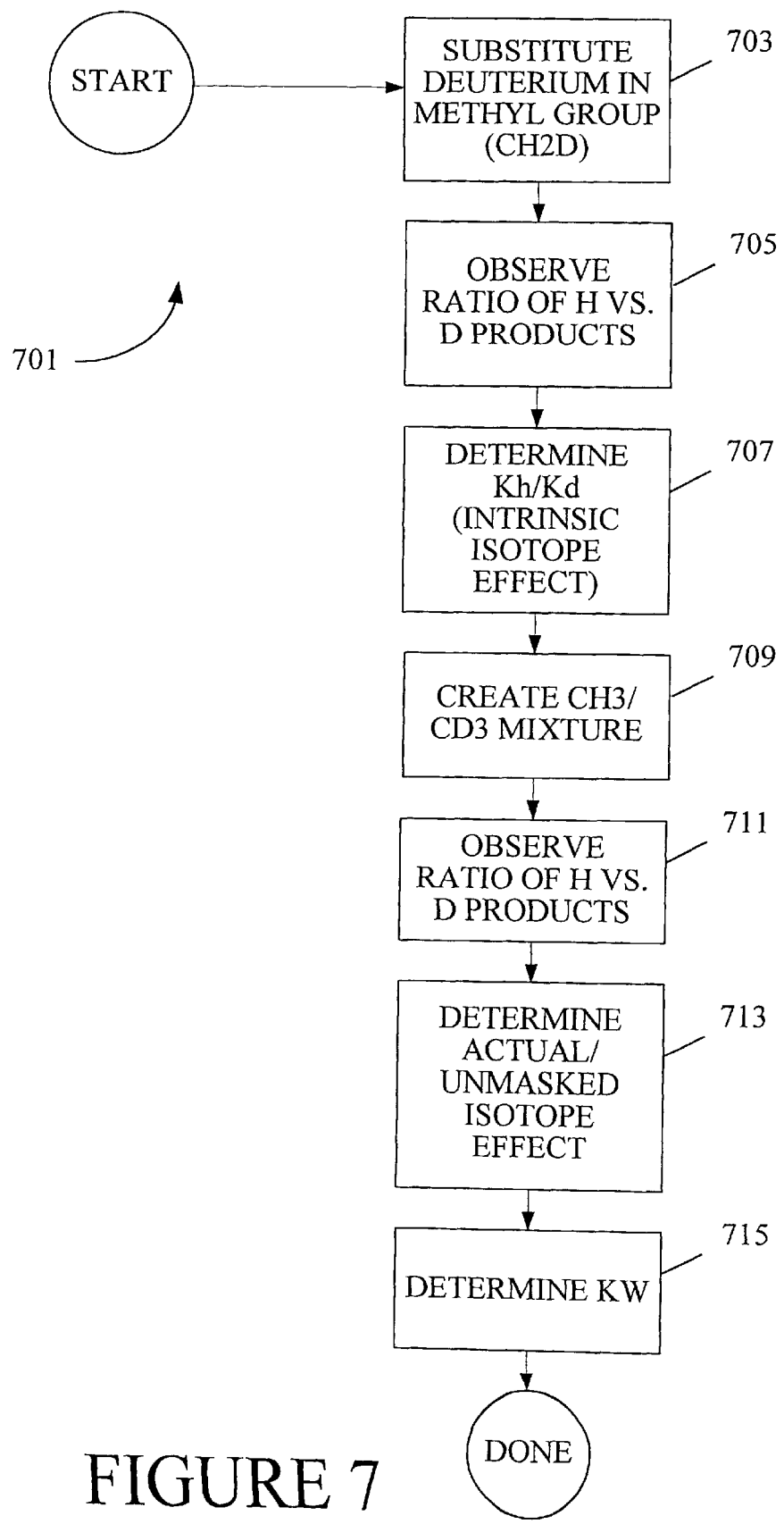
FIG. 7 is a flowchart for generating $K_W$. It is also applicable to generating other rate constants that are difficult or impossible to measure directly.

Direct determination of $k_W$ by stoichiometric measurement is of course difficult in an aqueous reaction medium. A method of indirection determination by the isotope effect can be used to measure rate constants such as $k_W$. FIG. 7 illustrates this process in a flowchart. See 701. First, the intrinsic, or intramolecular, isotope effect is determined for a reaction that is a branch reaction of the $k_W$. Typically, one hydrogen (H) of the reactive methyl group is substituted with one deuterium (D) atom. See 703. Then the ratio of products with hydrogen vs. deuterium is observed, which allows one to determine $k_H/k_D$, which is the intrinsic isotope effect. See 705 and 707. The $k_H$ will be larger than $k_D$ because the $E_A$ for deuterium abstraction is greater than that for hydrogen abstraction. The intrinsic isotope effect is typically determined with respect to step 707 of CYP catalytic cycle, but note that this is not strictly necessary. The presence of side reactions such as the water decoupling reaction also does not affect the value the intrinsic isotope effect.

Next, an intermolecular isotope effect, which is observed in the context of the reaction one wishes to indirectly measure, is determined. The intermolecular isotope effect is typically carried out using a mixture of the substrate that contains a mixture of $CH_3$ and $CD_3$ groups at the reactive site. If the reaction (in this example methyl group oxidation) is the rate-limiting step of the overall reaction, then the observed intermolecular isotope effect $[(V_D)](^D V)$ would be the same as the intrinsic isotope effect- the intrinsic isotope effect would be completely "unmasked." If the methyl group oxidation is not rate-limiting, then typically no isotope effect would observed, since the rate of formation of products with H or D would be the same. However, if there is a branch pathway such as water decoupling, as discussed above in the CYP catalytic cycle (step 112), then there would be a partial unmasking of the isotope effect. The greater that $k_W$ is with respect to $k_H$ or $k_D$, the greater the unmasking is. As $k_W \gg k_H$ or $k_D$, $V_D$ approaches $k_H/k_D$. The relationship between $[V_D]$ $^D V$ and the three relevant rate constants is:

$$^D V = \frac{\frac{k_H}{k_D} + \frac{k_H}{k_{alt} + k_w}}{1 + \frac{k_H}{k_{alt} + k_w}}$$

The $k_{alt}$ term of the equation accounts for other branch pathways which may be part of the overall reaction. Thus the remaining operations to determining $k_W$ are to create the mixture of $CH_3$ and $CD_3$, observe the ratio of H products v. D products, determine $[V_D]$ $^D V$ from this ratio, and determine the $k_W$ or other branch reaction from the formula above. See 709–715. The method of deriving a relationship between $^D V$ and the intrinsic isotope effect is well-known in the art, including this particular $^D V$ equation. Korzekwa and Gillette, "Overview: Theoretical Aspects of Isotope Effects on the Pattern of Metabolites Formed by Cytochrome P-450," Biological Reactive Intermediates IV, Witmer et al., Eds. Plenum Press, NY (1990); Korzekwa et al., "Theory for the Observed Isotope Effects from Enzymatic Systems that Form Multiple Products via Branched Reaction Pathways: Cytochrome P-450," Biochemistry: 28: 9012 (1989).

Using this equation, one can solve for $k_H/k_W$. By determining $k_H$ from molecular modeling, for example AM1, one can obtain $k_W$ and $E_A$ for water. Values for $E_A$ for water obtained by the above-described method are typically about 9–10.5 Kcal/mole, depending on the substrates used. Methods for obtaining values for $E_A$ for baseline hydrogen abstraction $E_A$ values are described in U.S. patent application Ser. No. 09/368,511 (Atty Docket No.: CAMIP001).

Once the substrate molecule, molecules, or class of molecules have been characterized in this manner, the researched can then decide upon a strategy to pursue with the substrate molecules. If we assume, as is typical, that the substrates have demonstrated ADME/PK properties that indicate they will metabolized too quickly, either in assays or in actual human/animal testing, then the researcher can decided whether to discard the substrate from further research and testing, or whether it is a good candidate for reengineering. The present invention identifies for the researches which reactive site or sites must be modified to change the metabolic properties of the substrate.

The present invention provides even more sophisticated tools for a researcher to analyze his or her results and develop further avenues for research. For example, as discussed above, a substrate with only one labile site is a good candidate for reengineering, since modification of that site will likely have a substantial effect on the overall rate of metabolism of the substrate. A substrate with even two or three sites will be substantially more difficult to reengineer, and a substrate with several sites will be impractical to reengineer. Such research decisions can be applied to whole classes and categories of substrates, since they will often share common characteristics, including common reactive sites. For example, the number of labile sites could be determined for a virtual combinatorial library, and problematic classes of molecules could be excluded pre-synthesis.

In another example, if a drug is too dependent on one pathway or if the primary pathway suffers from large variations in the population, the diversity of metabolism may want to be increased. Redesign candidates could be selected for compounds with increased lability. In another example, if a pathway is potentially toxic, the regioselectivity of metabolism could be altered to minimize this pathway.

These are just a few examples of how the information provided by the present invention can be used. Another example is the situation where the researcher wishes to design a drug with several reactive sites, to minimize possible drug-drug interactions. Armed with the information provided, the researched can make sophisticated decisions about how to design a substrate with several reactive sites and still maintain certain ADME/PK properties, although this generally will be a more difficult task than designing a drug with just a single reactive site with the desired properties.

Hardware and Software Implementation of the Invention

Figure 8A:
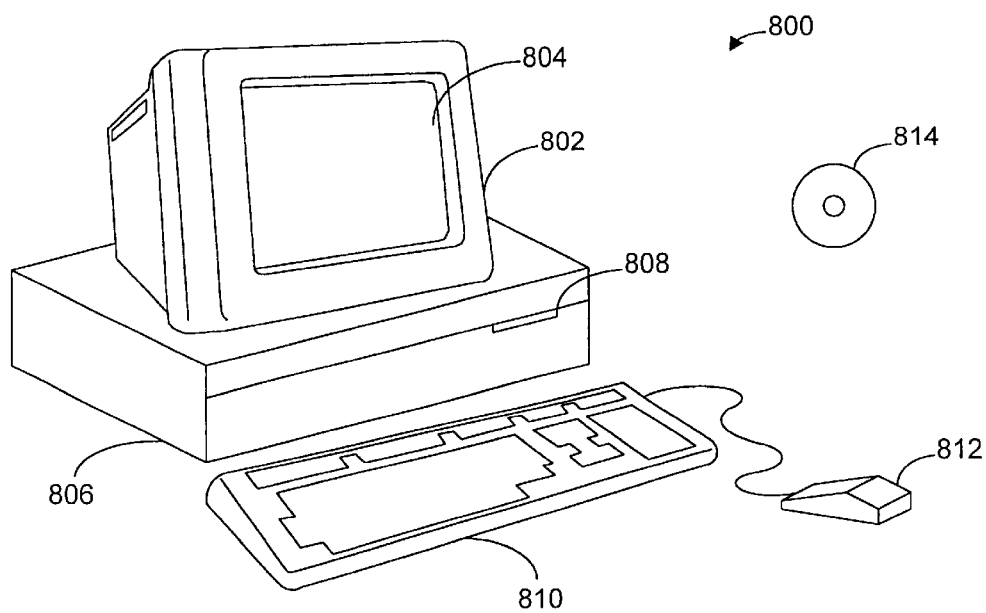
FIGS. 8A and 8B illustrate a computer system suitable for implementing embodiments of the present invention.
Figure 8B:
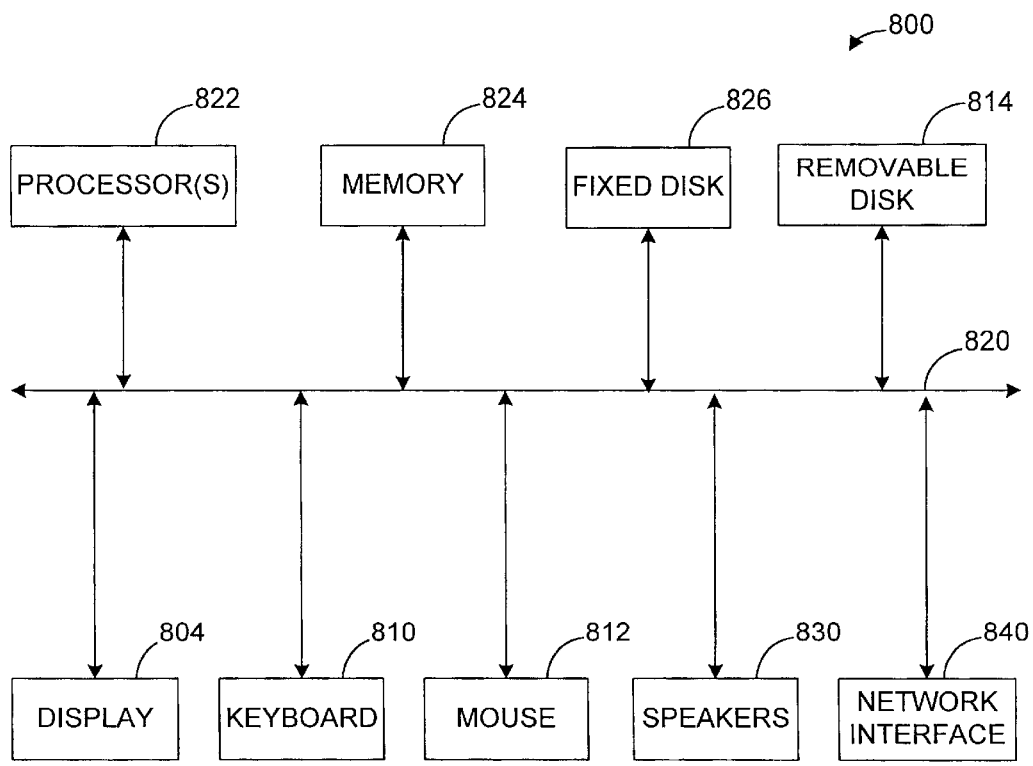

FIGS. 8A and 8B illustrate a computer system 800 suitable for implementing embodiments of the present invention. FIG. 8A shows one possible physical form of the computer system. Of course, the computer system may have many physical forms ranging from an integrated circuit, a printed circuit board and a small handheld device up to a huge super computer depending on the processing requirements of the embodiment. Computer system 800 includes a monitor 802, a display 804, a housing 806, a disk drive 808, a keyboard 810 and a mouse 812. Disk 814 is a computer-readable medium used to transfer data to and from computer system 800.

FIG. 8B is an example of a block diagram for computer system 800. Attached to system bus 820 are a wide variety of subsystems. Processor(s) 822 (also referred to as central processing units, or CPUs) are coupled to storage devices including memory 824. Memory 824 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 826 is also coupled bi-directionally to CPU 822; it provides additional data storage capacity and may also include any of the computer-readable media described below. Fixed disk 826 may be used to store programs, data and the like and is typically a secondary storage medium (such as a hard disk) that is slower than primary storage. It will be appreciated that the information retained within fixed disk 826, may, in appropriate cases, be incorporated in standard fashion as virtual memory in memory 824. Removable disk 814 may take the form of any of the computer-readable media described below.

CPU 822 is also coupled to a variety of input/output devices such as display 804, keyboard 810, mouse 812 and speakers 830. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 822 optionally may be coupled to another computer or telecommunications network using network interface 840. With such a network interface, it is contemplated that the CPU might receive information from the network, or might output information to the network in the course of performing the above-described method operations. Furthermore, method embodiments of the present invention may execute solely upon CPU 822 or may execute over a network such as the Internet in conjunction with a remote CPU that shares a portion of the processing.

In addition, embodiments of the present invention further relate to computer storage products with a computer-readable medium that have computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs), ROM and RAM devices, and signal transmission media for delivering computer-readable instructions, such as local area networks, wide area networks, and the Internet. Examples of computer code include machine code, such as produced by a compiler, and files containing higher level code that are executed by a computer using an interpreter. The invention also pertains to carrier waves and transport media on which the data and instructions of this invention may be transmitted.

Although various details have been omitted for brevity's sake, obvious design alternatives may be implemented. Therefore, the present examples are to be considered as illustrative and not restrictive, and the invention is not to be limited to the details given herein, but may be modified within the scope of the appended claims.

What is claimed is:

1. A computer-implemented method of characterizing a reactive site of a substrate molecule, the method comprising the operations of:
   a) determining a first activation energy or a first rate constant of a main reaction pathway at the reactive site of the substrate, while the substrate is complexed with an enzyme, to produce a product molecule; and
   b) comparing the first activation energy or the first rate constant of the main reaction pathway at the reactive site to a value of a second activation energy or a second rate constant of a branch decoupling reaction pathway of the substrate molecule in complex with the enzyme, which comparison facilitates a decision of whether or how to reengineer the substrate molecule.

2. The method of claim 1 wherein the branch pathway is a water decoupling reaction.

3. The method of claim 1, further comprising determining the effect of the reactive site on metabolism of the substrate molecule using information from at least one of (a) or (b).

4. The method of claim 1 wherein the enzyme is a cytochrome p450 enzyme.

5. The method of claim 1 wherein the substrate molecule is a compound under investigation as a drug candidate.

6. The method of claim 1 wherein the reactive site is an aliphatic carbon atom.

7. The method of claim 6 wherein the activation energy is calculated by the difference in free energy between the reactive site in its initial form and in its radicalized form with a hydrogen atom abstracted from it.

8. The method of claim 1 wherein the reactive site is an aromatic carbon atom.

9. The method of claim 8 wherein the activation energy is calculated by the difference in free energy between the reactive site in its initial form and in its radicalized form with a methoxy group attached to it.

10. The method of claim 1 wherein the activation energy is calculated using AM1.

11. The method of claim 1 wherein the characterizing further comprises binning the reactive site into three categories, stable, moderately stable, and labile.

12. The method of claim 11 wherein the stable category is defined as activation energies of approximately more than 0.5 kcal/mole greater than the activation energy of the branch pathway, the moderately stable category is defined as activation energies between approximately 1.5 kcal/mole less than and 0.5 Kcal/mole greater than the activation energy branch pathway, and the labile category is defined as activation energies approximately 1.5 kcal/mole less than the activation energy of the branch pathway.

13. The method of claim 1 wherein the branch pathway is a water decoupling reaction and the activation energy of the reaction is approximately 10 kcal/mole.

14. The method of claim 1 wherein the activation energy of the branch pathway is indirectly measured by an isotope effect measurement.

15. The method of claim 14, wherein the isotope effect measurement is the unmasking of a intrinsic isotope effect reaction using hydrogen and deuterium.

16. A computer system capable of characterizing a reactive site of a substrate molecule by comparing a reaction at the reactive site, resulting in generation of a product molecule, to a branch decoupling reaction of the substrate molecule in complex with an enzyme, the computer system comprising:
   one or more processors;
   one or more user input devices; and
   memory;
   wherein the processor and memory are configured to
      a) determine a first activation energy or a first rate constant of a main reaction pathway at the reactive site of the substrate molecule, while the substrate is complexed with the enzyme, to produce the product molecule; and
      b) compare the first activation energy or the first rate constant of the main reaction pathway at the reactive site to a value of a second activation energy or a second rate constant of a branch decoupling reaction pathway of the substrate molecule in complex with the enzyme.

17. The system of claim 16 wherein the branch pathway is a water decoupling reaction.

18. The system of claim 16, wherein the processor and memory are further configured to determine the effect of the reactive site on metabolism of the substrate molecule using information from at least one of (a) or (b).

19. The system of claim 16 wherein the enzyme is a cytochrome p450 enzyme.

20. The system of claim 16 wherein the substrate molecule is a compound under investigation as a drug candidate.

21. A computer-program product comprising a computer-readable medium and program instructions provided via the computer-readable medium, the program instructions comprising instructions for characterizing a reactive site of a substrate molecule by comparing a reaction at the reactive site, resulting in generation of a product molecule, to a branch decoupling reaction of the substrate molecule in complex with an enzyme, the instructions specifying:
   a) determining a first activation energy or a first rate constant of a main reaction pathway at the reactive site of the substrate molecule, while the substrate is complexed with the enzyme, to produce the product molecule; and
   b) comparing the first activation energy or the first rate constant of the main reaction pathway at the reactive site to a value of a second activation energy or a second rate constant of a branch decoupling reaction pathway of the substrate molecule in complex with the enzyme.

22. The computer-program product of claim 21 wherein the branch pathway is a water decoupling reaction.

23. The computer-program product of claim 21, further comprising instructions for determining the effect of the reactive site on metabolism of the substrate molecule using information from at least one of (a) or (b).

24. The computer-program product of claim 21 wherein the enzyme is a cytochrome p450 enzyme.

25. The computer-program product of claim 21 wherein the substrate molecule is a compound under investigation as a drug candidate.

* * * * *